US006774262B1

(12) United States Patent
Ikushima et al.

(10) Patent No.: US 6,774,262 B1
(45) Date of Patent: Aug. 10, 2004

(54) METHOD OF NOVEL NONCATALYTIC ORGANIC SYNTHESIS

(75) Inventors: Yutaka Ikushima, Miyagi (JP); Osamu Sato, Miyagi (JP); Kiyotaka Hatakeda, Miyagi (JP)

(73) Assignee: Japan as represented by Secretary of Agency of Industrial Science and Technology, Tokyo (JP)

( * ) Notice: Subject to any disclaimer, the term of this patent is extended or adjusted under 35 U.S.C. 154(b) by 0 days.

(21) Appl. No.: 09/659,821

(22) Filed: Sep. 11, 2000

(30) Foreign Application Priority Data

Sep. 13, 1999 (JP) ............................................ 11-259549

(51) Int. Cl.[7] .......................... C07C 51/235; C02F 1/68; C02F 1/00
(52) U.S. Cl. ........................ 562/531; 210/762; 210/763; 210/808
(58) Field of Search .......................... 562/531; 210/762, 210/763, 808

(56) References Cited

PUBLICATIONS

An et al, Applications of High–Temperature Aqueous Media for Syn. Org. Rxn., Apr. 18, 1997, J. Org. Chem. vol. 62., p. 2505–2511.*

Yutaka Ikushima, et al., "Solvent Effects on an Enzymatic Ester Synthesis in Supercritical Carbon Dioxide," Chemistry Letters, 1993, pp. 109–112.

Kiyotaka Hatakeda, et al., "Supercritical Water Oxidation of a PCB of 3–Chlorobiphenyl Using Hydrogen Peroxide," Chemistry Letters, 1997, pp. 245–246.

Yutaka Ikushima, et al., "An In Situ Raman Spectroscopy Study of Subcritical and Supercritical Water: The Peculiarity oh Hydrogen Bonding Near the Critical Point," Journal of Chemical Physics, vol. 108, No. 14, Apr. 8, 1998, pp. 5855–5860.

Yutaka Ikushima, et al., "Raman Spectral Studies of Aqueous Zinc Nitrate Solution at High Temperatures and at a High Pressure of 30 MPA," J. Phys. Chem. B, vol. 102, No. 16, Mar. 26, 1998, pp. 3029–3035.

* cited by examiner

*Primary Examiner*—Ba K. Trinh
*Assistant Examiner*—Taylor V. Oh
(74) *Attorney, Agent, or Firm*—Oblon, Spivak, McClelland, Maier & Neustadt, P.C.

(57) ABSTRACT

The invention provides a method of increasing the reaction rate of an organic synthesis reaction by utilizing supply of $OH^-$ from water in the absence of catalyst without adding a basic catalyst in supercritical water or subcritical water of at least 350 ° C., and a method of generating alcohol and carboxylic acid with high reaction rate by performing a Cannizzaro reaction in the absence of catalyst without adding a basic catalyst in supercritical water, and to a method of synthesis of alcohol and carboxylic acid from an aldehyde in the absence of catalyst without adding a basic catalyst near the critical point (375 to 380 ° C., 22.5 to 25 MPa) of supercritical water.

22 Claims, 3 Drawing Sheets

METHOD OF NOVEL NONCATALYTIC ORGANIC SYNTHESIS

BACKGROUND OF THE INVENTION

1. Field of the Invention

The present invention relates to a novel method of organic synthesis reaction in supercritical water that makes possible an organic synthesis reaction with high reaction rate under non catalytic conditions without adding high-concentration alkali, in supercritical water or subcritical water of at least 350° C. In more particular, the present invention relates to a method of performing an organic synthesis reaction by utilizing supply of OH⁻ from the water under non catalytic conditions in supercritical water or subcritical water of at least 350° C. and a method of increasing the reaction rate of this organic synthesis reaction, and to a method of generating alcohol and carboxylic acid by performing a Cannizzaro reaction under non catalytic conditions, in supercritical water, without adding a basic catalyst and a method of generating alcohol and carboxylic acid from an aldehyde under non catalytic conditions without adding a basic catalyst in the vicinity of the supercritical point.

2. Description of the Related Art

Recently, in the field of organic chemical reactions using a supercritical fluid as reaction medium, in addition to the various advantages in terms of the process, very considerable changes are reported in the reaction rate and selectivity in the vicinity of the critical point of the supercritical fluid (1 to 3: the numbers indicate prior art references, listed in the last, here and hereinbelow) and these have attracted considerable attention. A supercritical fluid has physicochemical properties intermediate those of a liquid and a gas, and the molecular kinetic energy is always dominant over the inter molecular forces. Nevertheless, in the vicinity of the critical point, the formation of order of the system due to inter molecular forces and its dispersal due to the kinetic energy of the molecules are in opposition, so, on the micro level, while some degree of order is maintained (formation of clusters), the molecules of these are in a state of rapid turnover. Consequently, in the vicinity of the critical point, slight changes of temperature or pressure produce large changes of fluid density.

In an organic synthesis reaction whose reaction medium is such a supercritical liquid, in regard to the reaction molecules, it has been discovered that the chemical interactions between different molecular species in the micro-regions surrounding these show specific changes in particular in the vicinity of the critical point (4 to 5), and it may be anticipated that changes of dynamic and static structure will considerably affect the equilibrium and rate of the reaction and the distribution of reaction products.

With this in view, the present inventors are striving to elucidate, on the molecular scale, the relationship between micro reaction fields and the factors that affect reactivity by developing new in situ measurement methods such as high-pressure FT-IR, UV/Vis, and Raman spectroscopy. If these can be put into practice, in addition to clarifying the relationship between reactivity and function of the reaction fields of the supercritical fluid, control of the micro reaction fields formed in the supercritical fluid by macro manipulation of temperature and pressure may be envisaged, and this may lead to the creation of novel chemical reaction processes of high selectivity and high efficiency which can also be applied industrially.

Whilst such application to the reaction fields of supercritical fluids is anticipated, in recent years, chemical reactions in which supercritical carbon dioxide and supercritical water are used to provide reaction fields have attracted attention. It is well known that, whereas carbon dioxide is non polar and its basic properties are scarcely changed in the supercritical condition, on changing to the supercritical condition, water shows completely different properties to water at ordinary temperature. For example, while the dielectric constant of water at ordinary temperature and atmospheric pressure is about 80, in the vicinity of the critical temperature, the dielectric constant of supercritical water is about 3 to 20, so the dielectric constant of water can be controlled continuously and in a wide range by means of temperature and pressure. The possibility therefore exists of dissolving organic substances of low polarity such as aromatic compounds, or various gases, in supercritical water; this is of exceptional value industrially.

Thus, oxidative decomposition reactions of toxic substances by utilizing this characteristic of supercritical water (SCWO) have attracted attention internationally (6). This is because supercritical water easily dissolves many organic substances (for example, chlorinated aromatic compounds) and oxidizing agents such as air or oxygen, making it possible to perform oxidative decomposition (combustion). The present inventors also have succeeded in complete decomposition of polychlorinated biphenyl (PCB) by SCWO, using hydrogen peroxide as oxidizing agent. Furthermore, the possibilities of application of supercritical water as a reaction medium for thermochemical reactions such as synthesis reactions, reduction reactions, thermal cracking reactions or dehydration reactions are very wide, clearly demonstrating its promise as a reaction solvent.

organic synthesis reactions in supercritical fluids have attracted attention, but most of these are chemical reactions employing an organo metallic catalyst in supercritical carbon dioxide (8); examples of organic synthesis reactions in which supercritical water is used as the reaction field are very few. The study of organic synthesis reactions in supercritical water is considered to be very significant on account of the properties of supercritical water that non polar compounds easily dissolve in supercritical water and that the critical temperature thereof is much higher than that of carbon dioxide.

Recent investigations (9, 10) have shown that the strength of the hydrogen bonds of water in the vicinity of the critical point is greatly reduced so that a dimer or monomer structure is produced. Furthermore, investigations (11, 12) by the present inventors of supercritical water or high-temperature, high-pressure aqueous solutions using Raman spectroscopy suggest that the monomer structure is further decomposed by structural instability (dynamic changes) in the vicinity of the critical point, with a strong probability that protons are generated. Generation of protons from the monomer structure of water suggests that OH⁻ ions (OH⁻ are simultaneously generated. If there are few sites for holding OH⁻ within the system, the local concentration of OH⁻ will rise, so considerable effects on chemical reactions may be anticipated.

As described above, various studies have previously been carried out centered on the vicinity of the critical point, concerning organic chemical reactions in supercritical fluids (carbon dioxide, water, ethane, or propane and the like) regarding temperature and pressure dependence of reaction rate and selectivity, from the point of view of the effects of physicochemical characteristics of the solvent, and the solvent or solute clustering effect. Furthermore, various studies have been made concerning the feasibility of creating novel chemical reactions including inorganic reactions or developing various chemical reactions in supercritical fluids in the presence of catalyst, or in situ methods of spectroscopic measurement of high-temperature/high-pressure reaction fields in for example supercritical water. If the relationship between chemical reactivity and micro factors in the region of the vicinity of the substrate molecules in a supercritical fluid can be elucidated on the molecular scale, this leads to elucidation of the reactivity and function of reaction fields in the supercritical condition and hence to the creation of reaction processes of high selectivity and high efficiency and can be expected to be of high utility from both the scientific and industrial viewpoints. However, at the present time, there are hardly any reports of examples of achieving high reaction rate by utilizing the supply of OH$^-$ from water in organic synthesis reactions in supercritical water.

In these circumstances, the present inventors, having previously recognized that the Beckmann rearrangement reaction proceeds in the absence of a catalyst in supercritical water, discovered that the reaction rate of an organic synthesis reaction can be increased by utilizing supply of protons from water in the absence of a catalyst in supercritical water, and that an extremely high rate constant is obtained by performing a pinacol rearrangement reaction in supercritical water, and, in addition to pinacolin, cyclic compounds are specifically generated in the vicinity of the critical point (375 to 380° C., 22.5 to 25 MPa). Furthermore, the present inventors, as a result of studying its feasibility by performing in situ observation of a non catalytic Cannizzaro reaction in supercritical water using high-temperature, high-pressure FTIR, discovered that the reaction using a basic catalyst proceeds non catalytically without the addition of a basic catalyst in supercritical water i.e. they discovered the feasibility of the supercritical water having a basic catalytic function, thereby perfecting the present invention.

Specifically, an object of the present invention is to provide a method of performing an organic synthesis reaction in the absence of a catalyst by utilizing the supply of OH$^-$ from the water in supercritical water, and to provide a method of increasing the reaction rate of this organic synthesis reaction.

Also, an object of the present invention is to provide a method of generating alcohol and carboxylic acid by performing a Cannizzaro reaction in the absence of catalyst without adding basic catalyst in supercritical water, and to provide a method of generating alcohol and carboxylic acid from aldehyde in the vicinity of the critical point.

SUMMARY OF THE INVENTION

According to the present invention, there is provided by a method of generating alcohol and carboxylic acid by a Cannizzaro reaction in supercritical water wherein an extremely high reaction rate is obtained without addition of high-concentration alkali.

The present invention relates to a method of increasing the reaction rate of an organic synthesis reaction by utilizing supply of OH$^-$ from water in the absence of catalyst without addition of basic catalyst in supercritical water or subcritical water of at least 350° C., and a method of generating alcohol and carboxylic acid at high reaction rate by performing a Cannizzaro reaction in the absence of catalyst without adding a basic catalyst in supercritical water, and a method of synthesis wherein alcohol and carboxylic acid are generated from aldehyde in the absence of catalyst without adding a basic catalyst in the vicinity of the critical point of supercritical water (375 to 380° C. 22.5 to 25 MPa).

DESCRIPTION OF THE INVENTION

In order to solve the above problems, the present invention comprises the following technical means:

(1) A method of non catalytic organic synthesis, which comprises performing an organic synthesis reaction by utilizing supply of OH$^-$ from water in the absence of catalyst without addition of basic catalyst in supercritical water or subcritical water of at least 350° C.

(2) A method of increasing the reaction rate of an organic synthesis reaction, which comprises performing the organic synthesis reaction by utilizing supply of OH$^-$ from water in the absence of catalyst without addition of basic catalyst in supercritical water or subcritical water of at least 350° C.

(3) The method according to above (1) or (2), wherein alcohol and carboxylic acid are generated by performing a Cannizzaro reaction in the absence of catalyst without addition of basic catalyst in supercritical water or subcritical water of at least 350° C.

(4) The method according to above (3), wherein alcohol and carboxylic acid are generated from an aldehyde in the absence of catalyst without addition of basic catalyst near the critical point.

The invention is further described in detail below.

On studying the feasibility of a Cannizzaro reaction in supercritical water, the present inventors discovered that alcohol and carboxylic acid are generated in the absence of catalyst without adding a basic catalyst, and that the reaction rate of an organic synthesis reaction is increased by supply of OH$^-$ from the water. In a conventional Cannizzaro reaction, for example potassium hydroxide or sodium hydroxide are added in high concentration, since unless alkali is added as catalyst, the reaction does not proceed. It is understood that the reaction is a reaction that is promoted by alkali i.e. OH$^-$ generated from alkali, since the reaction rate constant increases with increase of alkali concentration. By the present invention, it was discovered that a reaction which proceeds by basic catalysis proceeds in the absence of catalyst in supercritical water.

When a Cannizzaro reaction was performed in supercritical water, it was discovered that disproportionation occurs even in the absence of a catalyst, without adding a basic catalyst, causing alcohol and carboxylic acid to be generated. In a conventional Cannizzaro reaction, the reaction does not proceed unless a strong base such as sodium hydroxide is added as catalyst. For example, in the prior art method, an aqueous solution of sodium hydroxide of high concentration (2 mol/l) is added. The reaction rate constant is also increased as the alkali concentration increases, so it can be seen that the reaction is a reaction that is promoted by OH$^-$ generated from the alkali.

The present inventors have previously used the high-temperature, high-pressure Raman spectroscopy method to study the structure of supercritical water (water of critical temperature at least 375° C., critical pressure at least 22.05 MPa), and discovered that the hydrogen bonding structure is severely decomposed in the vicinity of the critical point, principally to a monomer or dimer structure. However, since there was no definite proof that the structure of water was broken down to protons (H+ or H$_3$O+) and OH$^-$, in order to verify this they first proposed and studied performance of a reaction to which protons or OH$^-$ contribute in supercritical water.

Accordingly, first of all, the strong possibility of protons being supplied from supercritical water was grasped by ascertaining that ε-caprolactam was generated by performing a Beckmann rearrangement reaction without adding acid in supercritical water, but, next, in order to obtain more reliable definite proof of supply of protons from water, the pinacol rearrangement reaction was studied (13, 14). Furthermore, since, if water molecule monomers are decomposed and protons generated OH⁻ also ought to be produced, in order to confirm this, a study was conducted to ascertain whether a Cannizzaro reaction could be achieved in supercritical water without, addition of alkali catalyst.

However, the remarkable increase in the rate constant obtained by performing the Cannizzaro reaction in supercritical water as illustrated in the embodiments, to be described, was completely unexpected. Although this depends on the alkali concentration and temperature of the reported examples that were compared, compared with the best previous results (NaOH 0.235 M, temperature 99.4° C., rate constant=9.4×10⁻² l.mol⁻¹ .s⁻¹) (15), an increase of reaction rate of more than 40 times was obtained. Also, although conventionally this reaction was conducted using, in addition, high-concentration 2 M aqueous solution of sodium hydroxide as catalyst, comparing the best result of the present inventors (reaction rate=3.90 l. mol⁻¹. s⁻¹) and the prior art case of 60° C. (rate constant=6.53×10⁻³ l.mol⁻¹ .s⁻¹), it was found that an increase of a factor of 600 times was obtained. Apart from IR, it was confirmed by NMR and GC-MS that no other reaction products than alcohol and carboxylic acid were generated.

Although the temperature of the above reaction is high since it is conducted in a supercritical condition (in a condition in which high-concentration alkali is added, performing the reaction at high temperature presents difficulties in regard to the equipment so, even if it is possible, considerable changes in the properties of the alkali may be anticipated), in view of the recent enhanced consciousness of environmental problems, it is considered that it is of great significance that a very high reaction rate is obtained without addition of high-concentration alkali, which has adverse effects on the environment. Also, only water, which is of low cost, being employed as solvent in the above reaction, and separation of the products being easy, this may be said to constitute a reaction method which is environment-friendly, in that no organic solvent is employed.

According to the present invention, it was found that a high reaction rate was obtained by performing the organic synthesis reaction in supercritical water utilizing supply of OH⁻ from the water in the absence of catalyst without adding high-concentration alkali.

Also, it was found that a very high rate constant was obtained in a Cannizzaro reaction in supercritical water.

Thus, the effectiveness of a method of performing an organic synthesis reaction by utilizing supply of OH⁻ from water in the absence of catalyst, without adding a basic catalyst, in the above supercritical water or subcritical water of at least 350° C. and of a method of increasing the reaction rate of an organic synthesis reaction and the like, has been first proved by the present inventors; consequently, the present invention is not restricted to a single specified method and any method of making use of these methods of course belongs to the method of the present invention, irrespective of its type.

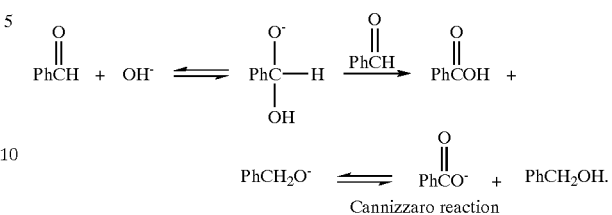

Scheme 1. Cannizzaro reaction

Explanation of the reference symbols
1 constituent element (Hastelloy C-276)
2 constituent element in which diamond window is fixed
3 molybdenum on which diamond window is mounted
4 diamond window

BEST MODE FOR CARRYING OUT OF THE INVENTION

EXAMPLES

Next, a specific description of the present invention is given with reference to examples; the following examples illustrate preferred embodiment of carrying out of the present invention, but the present invention is not restricted in any way to the following examples.

Example 1

(1) Outline of System

Figure 3:
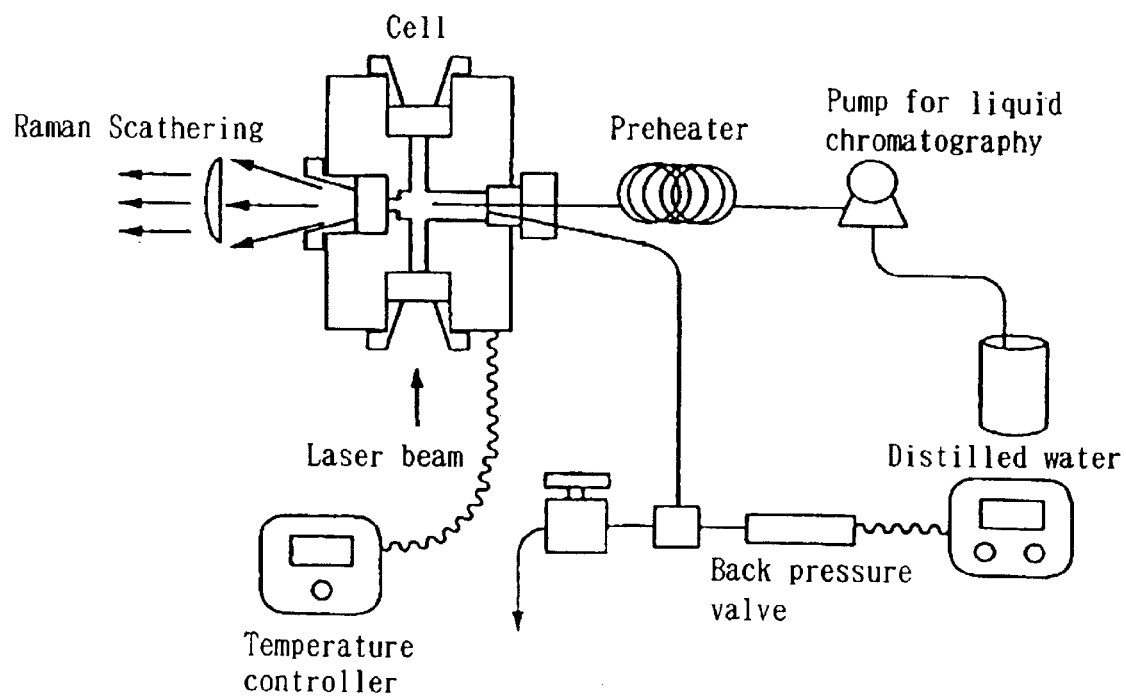
FIG. 3 shows a diagram of a continuous-flow type high-temperature and high-pressure laser Raman spectroscopy system.

FIG. 3 shows a diagram of a continuous-flow type high-temperature and high-pressure laser Raman spectroscopy system employed in this example. As the method of measurement, first of all, distilled high-purity water (distilled three times) was degassed by bubbling a large quantity of nitrogen gas through it, then filtered, and loaded into the cell continuously using a pump for an ordinary high-speed liquid chromatography. The pressure was controlled with an accuracy of ±0.1 MPa by a back pressure valve, and the temperature was controlled by a constructed mantle heater type heating furnace, with a temperature controller. The temperature calibration was validated by measuring the pressure at an arbitrary temperature (for example, 350° C.) in the vapor-liquid two phase equilibrium region, and comparing this temperature with the known temperature at the saturation point by referring to the NBC/NRC Table.

(2) Experimental Method

1) High-temperature and High-pressure Cell

Figure 1:
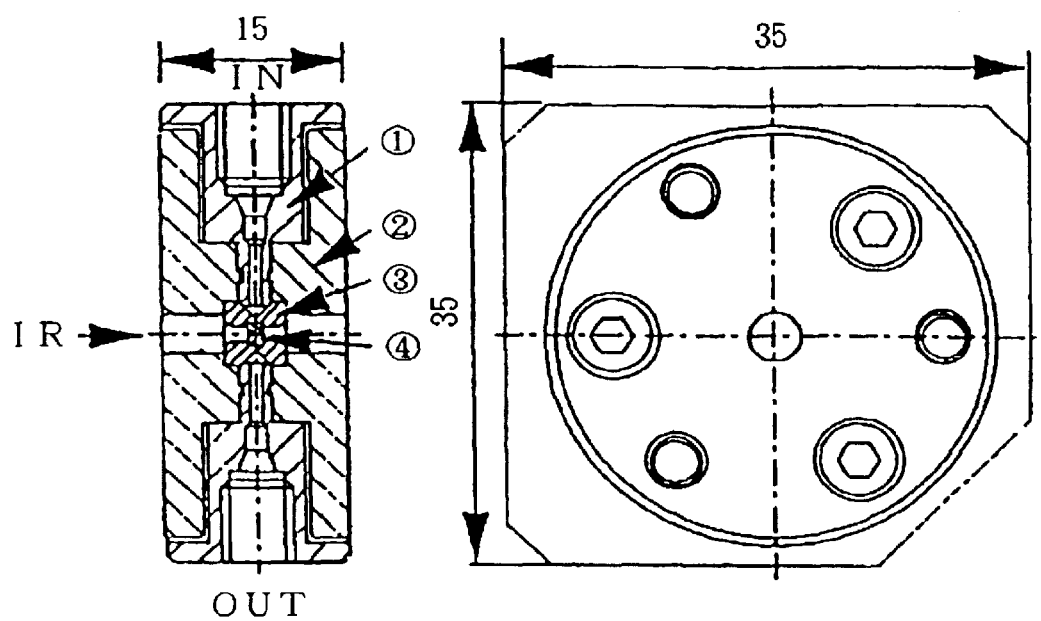
FIG. 1 shows a diagram of a high-temperature and high-pressure cell.

The continuous-flow type high-temperature and high-pressure FTIR system constructed by the inventors made possible continuous reaction in supercritical water and in situ observation using IR. FIG. 1 shows a diagram of a high-temperature and high-pressure cell. The use of diamond as the window material made it possible to measure the ordinary infra-red region. The optical path length of the cell was adjusted by using as spacer gold foil inserted between the diamond window and shock-absorbing member. The optical path length thereof was measured from the refractive index and the interference fringes of water, wherein pressure had no effect on this measurement, but the optical path length thereof increased with temperature, being 24.4 μm at 100° C., 44.0 μm at 400° C., and becoming fixed over 400° C. Also, the volume of the reaction portions (sum of the volume of the piping in the heating furnace and the path including the optical path within the cell) was 0.662 ml.

2) Method using the above system, the non catalytic Cannizzaro reaction of benzaldehyde in supercritical water was studied by in situ examination. An aqueous solution of benzaldehyde (concentration: 0.05 M) was prepared using distilled high-purity water that had been thoroughly degassed, and was loaded into the cell. continuously using a pump for liquid chromatography. The pressure was controlled by a back pressure valve and the temperature was controlled with an accuracy of ±1 K by a constructed vacuum superheating furnace. The high-temperature and high-pressure cell made it possible to measure the ordinary infra-red region by employing diamond as the window material. The optical path length of the cell was adjusted with a range of 20 to 44 μm by inserting gold foil as spacer next to the window material. The reaction was conducted under the conditions, wherein temperature of room temperature to 700 K, pressure of 0.1 to 25 MPa and exposure time (reaction time) of 12 to 360 seconds were adopted. In situ measurement of the reaction by IR was conducted with a resolving power of 4 $cm^{-1}$ after the prescribed temperature and pressure had been achieved.

(3) Results 1

Figure 2:
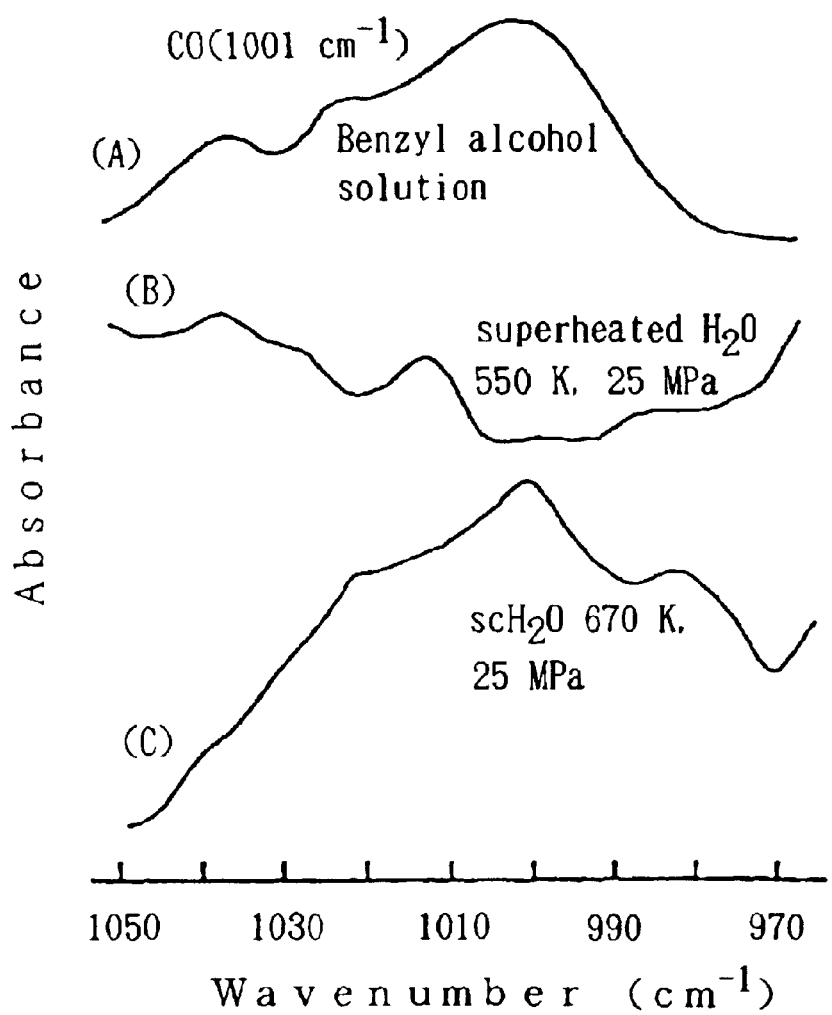
FIG. 2 shows an IR spectrum in the vicinity of 1000 cm⁻¹ of an aqueous solution of benzaldehyde.

Scheme 1 shows a Cannizzaro reaction; as is known, the reaction proceeds under basic catalysis and the reaction rate increases in proportion to the concentration of benzaldehyde and basic catalyst. FIG. 2 shows IR spectra in the vicinity of 1000 $cm^-$ of an aqueous solution of benzaldehyde measured with fixed pressure of 25 MPa, temperature 550 K (B), and pressure 25 MPa, temperature 670 K (C) and exposure time of 105 seconds. The maximum change was the point where strong absorption newly appeared at 1002 $cm^-$ in supercritical water (C). This coincided with the absorption of the stretching vibration of CO of benzyl alcohol shown in (A), so the fact that a redox reaction i.e. a Cannizzaro reaction of benzaldehyde was taking place in the absence of catalyst in supercritical water was thereby first discovered. Thus, $OH^-$ is generated from the supercritical water itself and contributes to the reaction. It is very interesting to confirm the fact that not only the Beckmann rearrangement reaction or pinacol rearrangement reaction, which proceed under acid catalysis, but also reactions that depend on basic catalysis can proceed non catalytically in supercritical water. It should be noted that it was confirmed not only by IR but also by GC-MS that benzoic acid is produced simultaneously with the benzyl alcohol. Furthermore, assuming that $OH^-$ is present in excess in the supercritical water, the pseudo second-order reaction rate constant ($k_2$) in relation to the benzaldehyde concentration was studied by the Lambert-Beer law. Then, assuming that the reaction mechanism of Scheme 1 is followed, since cross reactions do not take place and the production ratio of benzyl alcohol and benzoic acid is 1:1, the reaction rate of the benzaldehyde was determined from the rate of increase of optical absorption of the CO stretching vibration of benzyl alcohol. It was found that the relationship between the reaction rate and reaction time satisfied a pseudo second-order relationship. For example, the reaction rate of non catalytic reaction in the supercritical water at 25 MPa, 600 K is 0.29±0.1 $M^- s^{-1}$; which is much larger than $k_2=3.4\times10^{-2} M^{-1 s-1}$ when conducted at 373 K in an aqueous solution of 0.2 M NaOH methanol (15).

(4) Results 2

Next, the experimental conditions and the rate constants obtained according to the present invention are shown. The rate constants was treated assuming that alkali presented in excess the presence of excess alkali as same as in the other references, the reaction rate constant was treated as pseudo second-order with regard to the substrate concentration, and they were calculated from the rate of increase of the absorption frequency (CO stretching vibration) characteristic of benzyl alcohol produced by changing the temperature, pressure and exposure time of the benzaldehyde aqueous solution, using the continuous-flow type high-temperature and high-pressure FTIR device developed by the present inventors. It should be noted that, at temperatures lower than a temperature of 300° C., no benzyl alcohol was generated at any pressure for the exposure times (reaction times) indicated below i.e. it was not possible to confirm that a Cannizzaro reaction was proceeding. Recently, a Cannizzaro reaction of formaldehyde under hydrothermal conditions (temperature less than 250° C., pressure 4 MPa) has been reported, but these reaction conditions are completely different from those of the present invention and the reaction time is also extremely long (more than 1 hour) i.e. the reaction rate is slow, so it is believed that the reaction proceeds by a different mechanism under hydrothermal conditions.

1) Experimental conditions

Concentration of aqueous solution of aldehyde: 0.05 M
Temperature: 20° C.–427° C.
Pressure: 0.1, 19.1, 19.6, 20, 22.1, and 25 MPa
Exposure time: 10 seconds to 400 seconds
The aldehyde employed was benzaldehyde.

2) Results
(Pressure: 25 MPa)

| Temperature (° C.) | Rate constant ($l \cdot mol^{-1} \cdot s^{-1}$) |
|---|---|
| 352 | 0.073 |
| 367 | 0.145 |
| 377 | 0.287 |
| 387 | 0.468 |
| 397 | 0.830 |
| 427 | 3.900 |
| (Pressure: 22.1 MPa) | |
| 397 | 0.616 |
| 377 | 0.427 |
| 327 | $4.32 \times 10^{-3}$ |
| (Pressure: 19.6 MPa) | |
| 377 | 0.012 |
| (Pressure: 19.1 MPa) | |
| 377 | 0.015 |

Regarding previous research, there is an example of a synthesis reaction under hydrothermal conditions, but throughout the world there are scarcely any examples of synthesis reactions in supercritical water as described above; apart from the reactions of the present inventors, the only reaction that appears to have been studied is the Diels-Alder reaction in supercritical water. Incidentally there are many examples of reports of decomposition reactions in supercritical water.

Industrial Applicability

As described in detail above, the present invention relates to a method of increasing the reaction rate of an organic synthesis reaction by utilizing supply of OH⁻ from water in the absence of catalyst with no addition of basic catalyst in supercritical water, and to a method of generating alcohol and carboxylic acid by performing a Cannizzaro reaction and the like.

According to the present invention the outstanding advantages are obtained that:

(1) a redox reaction of aldehyde can be performed in the absence of catalyst without adding basic catalyst;
(2) the rate constant can be greatly increased by performing a Cannizzaro reaction in supercritical water;
(3) a very high reaction rate is obtained even without addition of high-concentration alkali;
(4) a Cannizzaro reaction is promoted non catalytically without addition of basic catalyst in supercritical water or subcritical water of more than 350° C.
(5) an organic synthesis reaction can be performed utilizing OH⁻ supplied from supercritical water; and
(6) a method of synthesis reaction can be provided which is environmentally friendly in that high-concentration acid and/or organic solvents are not employed.

Prior art references are indicated below.

1J. B. Ellington, J. F. Brennecke, J. Chem. Soc. Chem. Commun., 1094 (1993)
2Y. Ikushima, No. Saito, T. Yokoyama, K. Hatakeda, S. Ito, M. Arai, H. W. Blanch, Chem. Lett, 108 (1993)
3P. G. Jessop, T. Ikariya, R. Noyori, Science, 269, 1065 (1995)
4Y. P. Sun, M. A. Fox, K. P. Johnston, J. Am. Chem. soc., 114, 1187 (1992)
5A. A. Chialvo, P. G. Debenedetti, Ind. Eng. Chem. Res., 31, 1391 (1992)
6E. T. Ryan, T. Xiang, K. P. Johnston, M. A. Fox, J. phys, Chem., 1009365 (1996)
7K. Hatakeda, Y. Ikushima, S. Ito, O. Sato, N. Saito, Chem. Lett., 245 (1997)
8M. J. Burk, S. Feng, M. P. Gross, W. Tumas, J. Am. Chem. Soc., 117, 8277 (1995)
9N. Matsubayashi, C. Wakui, M. Nakahara, Phys. Rev. Lett., 78, 2573 (1997)
10M. M. Hoffmann, S. Conradi, J. Am. Chem. Soc., 119, 3811 (1997)
11Y. Ikushima, K. Hatakeda, N. Saito, M. Arai, J. Chem. Phys., 108, 5855 (1998)
12Y. Ikushima, N. Saito, M. Arai, J, Phys. Chem, B, 202, 3029 (1998)
13Ikushima, Y., et al., J. Org. Chem., 63, 9100 (1998)
14Ikushima, Y., et al., Angew. Chem. Int. Ed. Engl., in press (1999).
15Swain C. G. et al., J. Am. Chem. Soc, 101, 3576 (1979)

What is claimed is:

1. A method of non catalytic organic synthesis in a Carnizzaro reaction, or Beckmann rearrangement reaction that proceeds using OH⁻, which comprises performing said reaction in the absence of catalyst without addition of any basic catalyst in supercritical water or subcritical water of at least 350° C. with a reaction time of 10–400 seconds, utilizing a supply of OH⁻ from said water.

2. A method of increasing a reaction rate of an organic synthesis in a Cannizzaro reaction, or Beckmnann rearrangement reaction that proceeds using OH⁻, which comprises performing the organic synthesis reaction in the absence of catalyst without addition of any basic catalyst in supercritical water or subcritical water of at least 350° C. with a reaction time of 10–400 seconds, utilizing a supply of OH⁻ from said water.

3. The method according to claim 1, wherein alcohol and carboxylic acid are generated by performing a Cannizzaro reaction in absence of catalyst without addition of any basic catalyst in supercritical water or subcritical water of at least 350° C.

4. The method according to claim 2, wherein alcohol and carboxylic acid are generated by performing a Cannizzaro reaction in absence of catalyst without addition of any basic catalyst in supercritical water or subcritical water of at least 350° C. at a reaction time of 10–400 seconds, utilizing a supply of OH⁻ from said water.

5. The method according to claim 3, wherein alcohol and carboxylic acid are generated from an aldehyd in the absence of catalyst without addition of any basic catalyst near the critical point of the supercritical water.

6. The method according to claim 4, wherein alcohol and carboxylic acid are generated from an aldehyde in the absence of catalyst without addition of any basic catalyst near the critical point of the supercritical water.

7. The method as claimed in claim 1, wherein said reaction is performed in water at 375 to 380° C. and 22.5–25 MPa.

8. The method as claimed in claim 2, wherein said reaction is performed in water at 375 to 380° C. and 22.5–25 MPa.

9. The method as claimed in claim 3, wherein said reaction is performed in water at 375 to 380° C. and 22.5–25 MPa.

10. The method as claimed in claim 4, wherein said reaction is performed in water at 375 to 380° C. and 22.5–25 MPa.

11. The method as claimed in claim 1, wherein said reaction is performed in supercritical water.

12. The method as claimed in claim 1, wherein said reaction is performed in subcritical water of at least 350° C.

13. The method as claimed in claim 2, wherein said reaction is performed in supercritical water.

14. The method as claimed in claim 2, wherein said reaction is performed in subcritical water of at least 350° C.

15. The method as claimed in claim 3, wherein said reaction is performed in supercritical water.

16. The method as claimed in claim 3, wherein said reaction is performed in subcritical water of at least 350° C.

17. The method as claimed in claim 4, wherein said reaction is performed in supercritical water.

18. The method as claimed in claim 4, wherein said reaction is performed in subcritical water of at least 350° C.

19. The method according to claim 5, wherein the alcohol is benzyl alcohol, the carboxylic acid is benzoic acid, and the aldehyde is benzaldehyde.

20. The method according to claim 6, wherein the alcohol is benzyl alcohol, the carboxylic acid is benzoic acid, and the aldehyde is benzaldehyde.

21. The method as claimed in claim 1, wherein said reaction is performed in water at a pressure of at least 22.05 MPa.

22. The method as claimed in claim 2, wherein said reaction is performed in water at a pressure of at least 22.05 MPa.

* * * * *